(12) United States Patent
Meyn et al.

(10) Patent No.: US 6,566,329 B1
(45) Date of Patent: May 20, 2003

(54) FREEZE-DRIED PREPARATION OF HUMAN GROWTH HORMONE

(75) Inventors: Giorgio Meyn, Rungsted Kyst (DK); Hans Holmegaard Sørensen, Virum (DK); Thorkild Christensen, Allerød (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/594,103

(22) Filed: Jun. 14, 2000

Related U.S. Application Data
(60) Provisional application No. 60/141,372, filed on Jun. 28, 1999.

(51) Int. Cl.$^7$ .................. A61K 38/00; A61K 38/27
(52) U.S. Cl. ................. 514/12; 514/8; 514/21; 530/324; 530/338; 530/399; 530/420; 530/422
(58) Field of Search .................. 514/12, 8, 21; 530/324, 338, 399, 420, 422

(56) References Cited

U.S. PATENT DOCUMENTS

| | | | |
|---|---|---|---|
| 5,196,323 A | 3/1993 | Bodo et al. ............... | 435/69.51 |
| 5,589,167 A | * 12/1996 | Cleland ..................... | 424/85.7 |

FOREIGN PATENT DOCUMENTS

| | | |
|---|---|---|
| EP | 0 173215 A2 | 8/1985 |
| EP | 0 540 582 B1 | 8/1994 |
| WO | WO 97/02833 | 1/1997 |

OTHER PUBLICATIONS

Senderoff et al., "Consideration of Conformational Transitions and Racemization during Process Development of Recombinant Glucagon–like Peptide–1" Journal of Pharmaceutical Sciences, vol. 87, No. 2, Feb. 1998.*

"Somatropin" European Pharmacopoeia, 1997:0951, pp. 1518–1521.

D.E. Overcashier et al., "Preparation of Excipient–Free Recombinant Human Tissue–Type Plasminogen Activator by Lyophilization from Ammonium Bicar–bonate Solution: An Investigation of the Two–Stage Sublimation Phenomenon" Journal of Pharmaceutical Sciences. vol. 86, No. 4, pp. 455–459 (Apr. 1997).

* cited by examiner

*Primary Examiner*—Christopher S. F. Low
*Assistant Examiner*—Abdel A. Mohamed
(74) *Attorney, Agent, or Firm*—Reza Green, Esq.; Richard W. Bork, Esq.; Marc A. Began, Esq.

(57) ABSTRACT

A readily-soluble freeze-dried solid preparation of hGH with a minimal content of degradation products in terms of deamidation, dimers, polymers, and sulphoxide forms, obtainable by a method comprising a single lyophilization of an aqueous slurry of an amorphous hGH isoprecipitate, the slurry having a pH of from about 4.7 to 5.0 and being essentially free of buffer components other than acetate.

3 Claims, No Drawings

FREEZE-DRIED PREPARATION OF HUMAN GROWTH HORMONE

This application claims the benefit of provisional application No. 60/141,372 filed Jun. 28, 1999

FIELD OF INVENTION

The present invention relates to a method of preparing a freeze-dried preparation of human growth hormone.

BACKGROUND OF INVENTION

By recombinant DNA technology a great number of therapeutic proteins are produced and marketed. Dependent on the protein conformation and/or posttranslational modification a number of different host cell systems are used. Thus proteins like insulin, glucagon, factor VII and human growth hormone (hGH) are produced recombinantly. Following expression the desired proteins are purified, typically by use of a number of chromatographic operations and by means of precipitations. Precipitates can be crystalline or amorphous.

The final product achieved by a purification procedure is typically called bulk material to be used for the following formulation of the product. It is desirable to obtain crystalline bulk materials because crystals are well defined and easy to dissolve facilitating the following formulation procedure. Crystals are often stable and can therefore be stored safely before use.

Amorphous precipitates are typically achieved by precipitation at the isoelectric point in the presence of organic solvents such as ethanol in order to increase the yield, or by means of salting-out procedures by addition of ammonium sulphate.

hGH has previously been isoprecipitated as an amorphous solid. However, it is generally difficult to redissolve amorphous hGH completely. To achieve total dissolution it is necessary to use denaturing buffers such as guadinium chloride or urea.

Experience has shown that it is very difficult to crystallize hGH. HGH can be co-crystallized with zinc ions giving small crystals (European Patent No. 540 582: Growth Hormone Crystals and a Process for Production of these GH-Crystals, Applicant: Novo Nordisk A/S, Inventors: Junker, J.; Skriver, L.). However, formulations of hGH typically do not have the presence of zinc ions. Therefore, before formulation, hGH co-crystallized with zinc has to be redissolved and a buffer change has to be performed.

A solid hGH product—SOMATROPIN—is mentioned in pages 1518–1521 of the 1997 European Pharmacopoeia (1997:0951). How to prepare this bulk material is not mentioned and only specifications are stated.

In 1997, Overcashier et al. (Overcashier D. E. et al., Jour. Pharm. Sci. 86(4):455–459 (1997)) published an article describing the preparation of excipient-free recombinant human tissue-type plasminogen. The article states that precipitation of proteins by pH adjustments (iso-precipitation) or ionic strength regulation often leads to denaturation of the proteins resulting in reduced therapeutic activity. A method based on lyophilization of the protein from the ammonium bicarbonate was described. It was shown that the freeze-drying procedures took place in two steps. A large pressure increase was observed in the procedure when water was removed, and it was suggested that ammonium bicarbonate was evenly distributed over the lyophilization product. The following sublimation of ammonium bicarbonate resulted in a decomposition into water, carbon dioxide and ammonia which gave rise to the mentioned pressure increase. Thus, in the presence of ammonium bicarbonate it can be technically difficult to perform the freeze-drying procedure which might give reproducibility problems for the solid bulk material.

In 1998, Senderoff et al. (Senderoff, R. I. et al., Jour. Pharm. Sci. 87(2):183–189 (1998)) described a method to achieve excipient-free GLP-1 (glucagon-like peptide 1). It starting material was obtained by reverse phase chromatography in ethanolic acetic acid buffers followed by isoprecipitation, resolubilisation and a first lyophilization. However, redissolution in neutral buffer systems was highly unsatisfactory. Furthermore, the conformation was different from that of a standard. To improve dissolution and to achieve the correct conformation (stability) the first lyophilisate was reprocessed in three different ways:

1) Wash followed by lyophilization of a slurry.
2) Resolubilisation in 0.05 M ammonium hydroxide followed by lyophilization.
3) Resolubilisation in 6 M urea 1% acetic acid—reverse phase chromatography—cation exchange chromatography, elution with 0.05 M ammonium hydroxide—lyophilization.

To compare the conformations of the lyophilised GLP-1 products infrared spectroscopy was used. Only procedure 3 resulted in a product that could readily be resolubilised completely and had the same conformation as that of a standard preparation.

The other methods showed considerable conformational deviations from that of the standard and unsatisfactory dissolution properties.

In spite of the above teachings it has now surprisingly been shown that a single lyophilization of a slurry of an amorphous hGH precipitate in an aqueous system (free of buffer components) at the isoelectric point resulted in a product with a minimal content of degradation products in terms of deamidation, dimers, polymers, etc. and also with a correct tertiary structure as determined by NMR spectroscopy. Additionally, the product was readily soluble in neutral buffers and full biological activity was encountered.

SUMMARY OF THE INVENTION

The present invention provides a method for preparing a readily soluble freeze-dried solid preparation of hGH with a minimal content of degradation products in terms of deamidation, dimers, polymers, and sulphoxide forms, the method comprising a single lyophilization of an aqueous slurry of an amorphous hGH isoprecipitate, the slurry being essentially free of buffer components and having a pH of or near to the isoelectrical point of hGH (pH about 5).

The present invention further provides a readily soluble freeze-dried solid preparation of hGH with a minimal content of degradation products in terms of deamidation, dimers, polymers, and sulphoxide forms, obtainable by a method comprising a single lyophilization of an aqueous slurry of an amorphous hGH isoprecipitate, the slurry being essentially free of buffer components and having a pH of or near to the isoelectrical point of hGH.

The freeze-dried solid preparation of hGH is readily soluble in aqueous buffer.

DETAILED DESCRIPTION OF THE INVENTION

In order to obtain a uniform hGH bulk material a solid hGH preparation was prepared essentially free of excipients.

To obtain this, freeze-drying was carried out at low pH (approximately 5) close to the isoelectric point of hGH. Before freeze-drying the pH was adjusted with acetic acid, thus the only counter ion present was acetate buffering at pH 5. Freeze-drying at fairly low pH has the advantage that the formation of degradation products are minimised and a more homogeneous product is obtained in comparison with freeze-drying carried out at higher pHs such as in the carbonate containing systems.

The hGH solid bulk is prepared as follows:

The starting material for the production of solid bulk hGH is the product from the last step of the purification process used for purifying recombinantly produced hGH.

The process steps are designed to transform the hGH solution into a freeze-dried powder without or almost without excipients.

The hGH solid bulk preparation consists of a concentration step, a desalting step, a microfiltration step, an isoprecipitation step, and a freeze-drying step.

The concentration step: The step has been introduced in order to concentrate the hGH solution from, for example, 2–6 mg/ml to 20–70 mg/ml, and to obtain a buffer change from, for example, 7 M urea buffer to 0.35 M ammonium acetate buffer. The concentration is performed on an anion exchange column.

The desalting step: The step has been introduced in order to obtain hGH in pure water without salts and other excipients. The desalting is performed on a desalting column.

The microfiltration step (0.22 μm filter): The step has been introduced in order to minimise the microbial contamination. Sterility is not claimed.

The isoprecipitation step: The step has been introduced to stabilise the product during the final freeze-drying. The solution was precipitated by adjusting the pH to 4.7–5.0 with 1 M of acetic acid (and eventually ammonia, if necessary to further adjust the pH).

The freeze-drying step: The step has been introduced in order to obtain a hGH solid bulk powder that is nearly 100% somatropin and which is easy to dissolve in aqueous buffer.

All finished hGH products can be manufactured from the hGH solid bulk of the present invention.

HGH prepared as described above will result in a bulk product
a) which dissolves readily in aqueous buffers at pH 7–8;
b) having a water content of about 0.5 to about 2%;
c) having a total content of polymeric and dimeric forms of hGH of about 0.5 to about 2%;
d) having a content of sulphoxide forms of hGH of from about 0.3 to about 0.8%;
e) having a content of acetate of approximately 1%, or less;
f) having a content of desamido forms of from about 0.6% to about 1%; and
g) having a low content of other degradation products, such as spitforms, and cyclic imides.

The isoelectrical point of hGH is found at a value of pH 4.9, thus a pH value of from 4.7 to 5.0 may suffice to isoprecipitate the human growth hormone.

The following examples are offered as an illustration of the invention, not as a limitation.

EXAMPLES

Example 1

The starting material was hGH dissolved in 7 M urea buffer at a hGH concentration of 2–6 mg/ml.

1) The solution was desalted on a desalting column followed by
2) a concentration step by ultrafiltration.
3) The concentrated solution was microfiltrated through a 0.22μ filter to obtain a clear solution with a reduced microbial level.
4) The filtered solution was desalted on a G25 Sephadex column in water resulting in an excipient-free hGH solution with pH about 7.
5) The hGH solution was freeze-dried to obtain hGH powder with a residual water content of from about 0.5 to about 2%.

The hGH powder obtained had a high content of dimeric hGH (=2.2%)

The freeze-dried powder was fluffy and electric and very difficult to handle as it generated hGH dust to the environment.

Example 2

The starting material was the same as described in example 1.

1) The solution was desalted on a desalting column followed by
2) a concentration by ultrafiltration.
3) The concentrated solution was microfiltrated through a 0.22μ filter to obtain a clear solution with a reduced microbial level.
4) The filtered solution was applied on a G25 Sephadex column in water to obtain an excipient-free hGH solution.
5) The product was isoprecipitated at pH 4.9 by adjusting with 1 M HCl solution. The isoprecipitated hGH was isolated by centrifugation.
6) The centrifuged hGH was freeze-dried to a residual water content of from about 0.5 to about 2%.

The hGH powder obtained had a satisfactory content of dimeric hGH (=0.8%). The sulphoxide content of 0.9% was considered to be too high. Furthermore, the loss of product (=40%) during the centrifugation was unacceptable high.

Example 3

The starting material was the same as described in example 1.

In order to increase the process yield during the isoprecipitation step and centrifugation step ethanol was added to decrease the solubility.
(Steps 1–4 remain the same as in example 2.)

1) The solution was desalted on a desalting column followed by
2) a concentration by ultrafiltration.
3) The concentrated solution was microfiltrated through a 0.22μ filter to obtain a clear solution with a reduced microbial level.
4) The filtered solution was applied on a G25 Sephadex column in water to obtain an excipient-free hGH solution.
5) Ethanol was added to the desalted aqueous solution of hGH to a concentration of from about 28 to about 30% of the final solution.
6) The product was isoprecipitated by adjusting the pH to 4.9 with 1 M HCl solution. The isoprecipitated hGH was isolated by centrifugation.
7) The centrifuged hGH was freeze-dried to a residual water content of from about 0.5 to about 2%.

The hGH powder obtained had an unacceptable high content of dimeric hGH (=1.9%) and of polymeric hGH (=4.9%). Loss of product during the isoprecipitation and centrifugation was 10%.

Example 4

The starting material was the same as described in example 1.

In the isoprecipitation step the pH is adjusted with 1 M acetic acid solution.

In order to avoid product loss, the combined mixture of isoprecipitated hGH and the supernatant hGH was freeze-dried as a slurry to a residual water content of from about 0.5 to about 2%.

1) The solution was desalted on a desalting column followed by
2) a concentration by ultrafiltration.
3) The concentrated solution was microfiltrated through a 0.22μ filter to obtain a clear solution with a reduced microbial level.
4) The filtered solution was applied on a G25 Sephadex column in water to obtain an excipient-free hGH solution.
5) Ethanol was added to the desalted aqueous solution of hGH to a concentration of from about 28 to about 30% of the final solution.
6) The product was isoprecipitated by adjusting the pH to 4.9 with 1 M acetic acid solution.
7) The combined mixture of isoprecipitated hGH and the supernatant hGH was freeze-dried as a slurry to a residual water content of from about 0.5 to about 2%.

The content of dimeric hGH was 0.4%. The content of polymeric hGH was <0.2% and the content of sulphoxide forms of hGH was 0.4% which is considered acceptable.

The same freeze-drying process was used in all four examples

The freeze-drying process was composed of a freezing step, a primary drying step, and a secondary drying step. The freeze-drying process was designed to obtain a desired low level of residual water (from about 0.5 to about 2%).

The solutions to be freeze-dried in the examples does not contain gas-evolving buffer excipients (for example $NH_4^+$, $CO_3^{2-}$). Therefore, pressure increase during the freeze-drying process was not observed.

The hGH powder obtained by freeze-drying of the iso-precipitated slurry resulted in a free-flowing and non-electric powder with good handling properties. Surprisingly, the homogeneity and reproducibility of the freeze-drying of a slurry were highly satisfactory.

What is claimed is:

1. A method for preparing a soluble freeze-dried solid preparation of hGH having a) a total content of polymeric and dimeric forms of human Growth Hormone (hGH) of about 0.5 to about 2%;
   b) a content of sulphoxide forms of hGH of from about 0.3 to about 0.8%; and
   c) a content of desamido forms of from about 0.6% to about 1%;

said method comprising a single lyophilization of an aqueous slurry of an amorphous hGH isoprecipitate, the slurry having a pH of from about 4.7 to 5.0.

2. The method of claim 1, further comprising before the isoprecipitation and lyophilization steps, a desalting step and the subsequent addition of ethanol to the desalted aqueous solution of hGH to a concentration of from 28 to 30% of the final solution, and a subsequent adjustment of the pH to 4.7–5.0 using acetic acid.

3. The method of claim 2, wherein the pH after being adjusted with acetic acid is further adjusted to 4.7–5.0 using ammonia.

* * * * *